United States Patent [19]

Hajianpour

[11] Patent Number: 4,955,947
[45] Date of Patent: Sep. 11, 1990

[54] PRESSURE SENSOR

[75] Inventor: Mohammed A. Hajianpour, Miami, Fla.

[73] Assignee: Ace Orthopedic Manufacturing, Los Angeles, Calif.

[21] Appl. No.: 50,506

[22] Filed: May 14, 1987

[51] Int. Cl.$^5$ .............................................. A61B 5/00
[52] U.S. Cl. ...................................... 128/748; 73/744
[58] Field of Search .................... 128/672–675, 128/748; 73/715, 744

[56] References Cited

U.S. PATENT DOCUMENTS

| | | | |
|---|---|---|---|
| 3,720,201 | 3/1973 | Ramsey, III | 128/673 X |
| 3,901,083 | 8/1975 | Wallace | 73/715 |
| 3,920,002 | 11/1975 | Dye et al. | 128/748 |
| 4,003,370 | 1/1977 | Emil et al. | 128/673 |
| 4,164,938 | 8/1979 | Patton | 128/748 X |
| 4,252,131 | 2/1981 | Hon et al. | 128/748 |
| 4,501,142 | 2/1985 | Huang | 73/715 |
| 4,655,749 | 4/1987 | Fischione | 128/748 X |
| 4,727,887 | 3/1988 | Haber | 128/748 |

Primary Examiner—Angela D. Sykes
Attorney, Agent, or Firm—Grant L. Hubbard

[57] ABSTRACT

A tissue pressure measuring system is disclosed. The system includes a syringe with a cylindrical passage and means for connecting a tissue invasion device in fluid communication with the cylindrical passage. A plug is present within the cylindrical passage and has a diaphragm therein.

1 Claim, 2 Drawing Sheets

PRESSURE SENSOR

FIELD OF THE INVENTION

This invention relates to medicine and surgery generally and, in particular, to instruments for use in the practice of medicine and surgery and, with greater particularity, to an instrument for measuring tissue pressure.

BACKGROUND OF THE INVENTION

Increased tissue pressure is a pathogenic factor in the compartmental syndrome. The primary goal in treating this condition is the prompt lowering of tissue pressure to normal. Surgical release must not only decompress the contents of the compartment but also accommodate any postischemic swelling occurring after the decompression procedure. The general background of compartmental syndrome, and various procedures for treating compartmental syndrome, including the relief of pressure, are described by Dr. Frederick A. Matsen, III, Clinical Orthopedics and Related Research, No. 113, November-December, 1975. There are also many other journal publications and treatices which discuss this syndrome and methods of treatment.

The reduction of tissue pressure using a syringe to remove fluid from the tissue zone.. under compression, accompanied by the measurement of tissue pressure, is one of the techniques used in treating intracompartmental syndrome. Instruments for accomplishing this purpose are manufactured and distributed by various manufacturers. For example, Howmedica, Inc., Orthopedics Division, 359 Veterans Boulevard, Rutherford, New Jersey 07070, distributes and sells the Howmedica Slit Catheter System, and Intermedics Orthopedics Inc., 6968 Sierra Court, Dublin, California 94568, distributes an intracompartmental pressure monitoring system with a Wick Catheter. Both of these systems and other systems generally involve a syringe with the usual distal connection for a needle, Wick Catheter or the like for insertion into the tissue and removal of liquid. In addition, some kind of instrument is provided, usually a rather bulky instrument which necessarily rests on a table, shelf or another location occupying space and interfering with freedom of movement of the surgeon. It is a feature of this invention to provide an intracompartmental pressure measuring system for use in treating intracompartmental syndrome.

SUMMARY OF THE INVENTION

The invention described and claimed herein comprises the combination of a syringe with means for connecting the syringe to a needle or Wick Catheter, or other means for introduction of or removal of fluid from tissue, a pressure transducer, an instrument mounted in the syringe, the entire assembly being suited to being held by the hand of the surgeon, or the user.

The present invention comprises, as a combination, a tissue pressure measuring system comprising a syringe comprising a cylindrical passage and means for connecting a tissue invasion plug in the cylindrical passage having a passage formed therethrough, means such as, for example "O" rings or simply lubricant, sealing the periphery of the plug in fluid tight moveable relationship with the interior of the cylindrical passage; a resilient pressure transmitting diaphragm sealing the passage through the plug, and a cylindrical pressure measuring instrument connected to the plug for moving the plug in the cylindrical passage and for sensing pressure transmitted through the diaphragm. The instrument preferably comprises a pressure transducer, a microprocessor and a plurality of light-emitting diodes, or equivalent visual display devices, and means interconnecting and powering the same for lighting, in sequence, the light-emitting diodes as the pressure transmitted through the diaphragm is increased.

DESCRIPTION OF THE PREFERRED EMBODIMENT

It will be understood that the following description is intended merely to exemplify and describe the preferred embodiment of the invention and does not limit the scope thereof.

Figure 1:
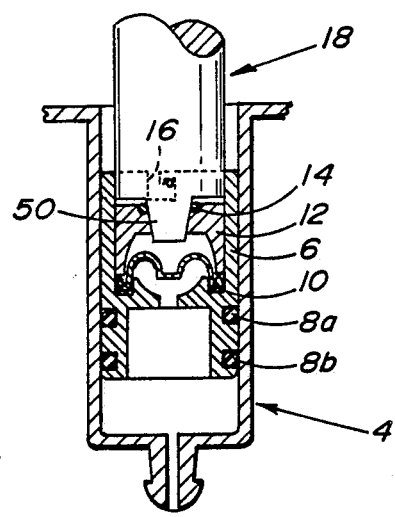
FIG. 1 is an assembly drawing of the entire system of this invention, shown in partial cutaway cross section for clarity.

Referring first to FIG. 1, the invention comprises the assembly or combination of a syringe 4, which is or may be of a conventional type with conventional means for being connected to a needle or Wick Catheter or other tissue infusion or fluid removal device.

Slidably received inside the syringe is a plug 6 which is sealed by means of "O" rings 8A and 8B in the interior of the syringe. The plug 6 can be moved inwardly and outwardly in the manner that the syringe plunger is usually operated.

Figure 2:
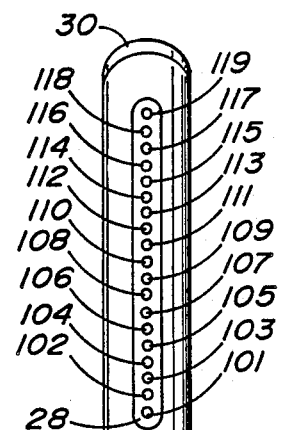
FIG. 2 is a perspective view of the instrument portion of this invention.
Figure 3:
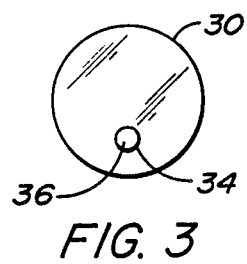
FIG. 3 is a cross-section of the instrument.
Figure 4:
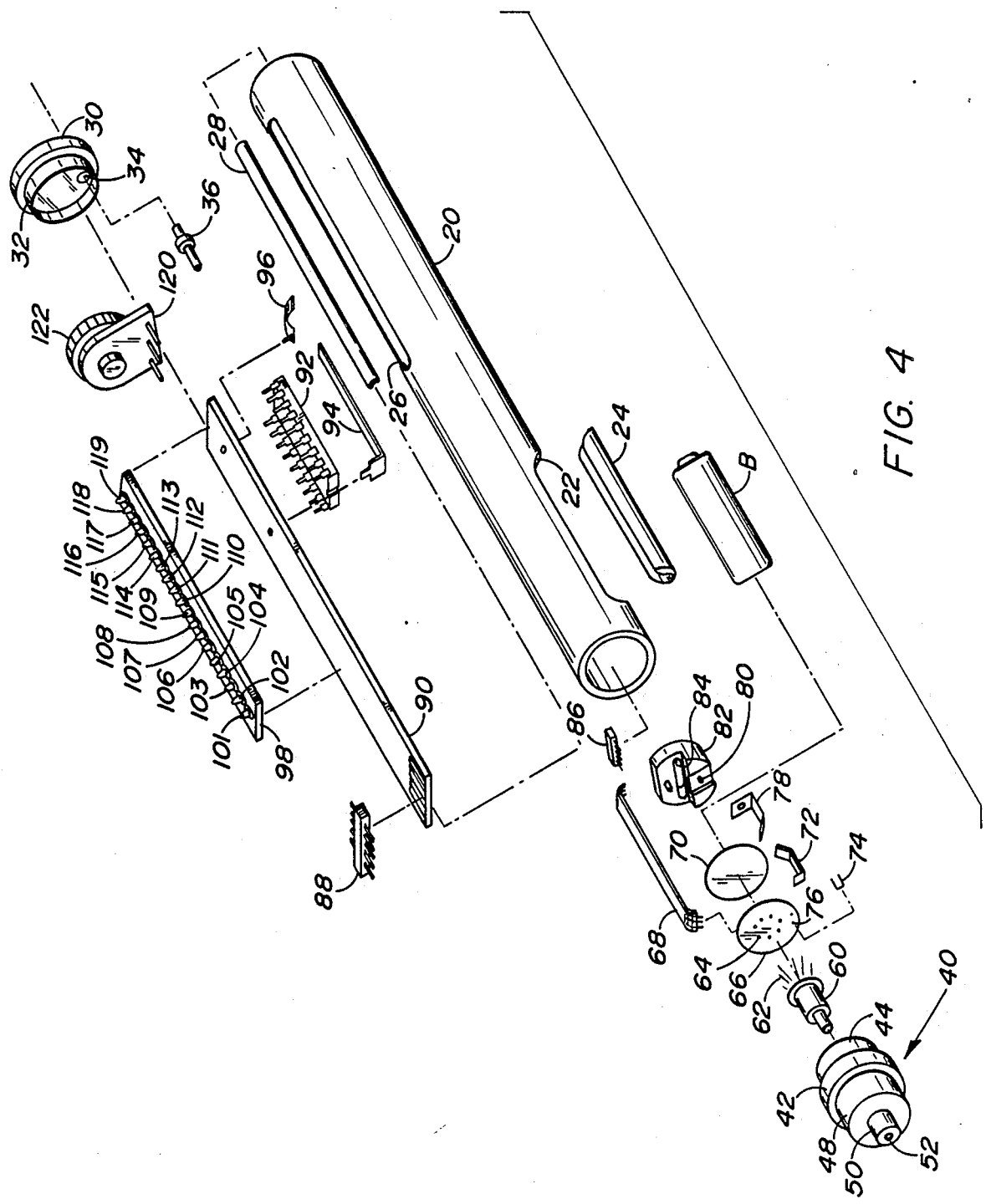
FIG. 4 is an exploded view of the instrument of this invention showing the components thereof.

A membrane of silicone rubber, or other suitably inert resilient material 10 is fitted into the interior of the plug 6, which is hollow in that it provides fluid passage therethrough, the membrane sealing off the passage through plug 6. As clearly shown in the drawing, the diaphragm is a membrane formed of an inert resilient material fitted inside the interior of the plug. The diaphragm has a substantially flat center portion and an annular portion which a substantially arcuate cross-section around the center portion. A plug 12, which also has a passage in it, has an annular flange which fits around the periphery of the membrane and seals the membrane in the plug 6. Adjacent to the passage through the plug 12, an "O" ring 14 may be provided which seals the instrument as it is inserted into the syringe. The instrument 18, which will be described in greater detail, is held in the syringe by means of a bayonet fitting shown in dashed lines at 16. It will be clearer, now, from the drawing and the above description that the instrument 18 may be used to introduce fluid into the tissue or to remove fluid from the tissue. Pressure is transmitted through the membrane 10 to the measuring instrument 18 which will now be described, making particular reference to FIGS. 2 and 3.

The instrument 18 comprises a generally cylindrical sleeve 20 with an opening 22 through which a battery B may be inserted and which is closed with a cap 24 which may be held in place by detents, screws, or in any other desired way. Another elongate aperture 26 is formed which is covered with a transparent film 28 of clear polycarbonate or other suitable material. The clear material forms a window over the aperture 26 through which light-emitting diodes (LED's) may be viewed, as will be described.

The distal end of the cylinder 20 is closed by cap 30 which is provided with a flange 32 which fits snugly down into the cylinder 20 and has an aperture 34 therethrough which receives a button 36, the distal end of which may be operated by the surgeon and which forms part of an electrical switch to turn on the instrument to give a measurement.

At the proximal end of the instrument, a plug 40 is provided which closes the end of the instrument, but for an aperture which permits the instrument to sense pressure, the plug 40 being equipped with a sleeve 42 and a flange 44, the flange 44 fitting snugly inside the cylinder 20. Another flange 48 and an apertured insert 50, the aperture being shown at 52 in the Figures, are provided, forming the extreme proximal end of the instrument. A pressure transducer 60 is in fluid communication with the passageway 52. The pressure transducer 60 may be of any desired type, the strain gauge type being most convenient and suitable. One particularly convenient and available transducer is a transducer identified by part number NPH-5-03G, identified as a Novasensor, manufactured by Novatronics of Fresno, California. This particular sensor is accurate in the pressure range from 0 to 5 pounds per square inch gauge pressure (PSIG). It is to be emphasized that this designation and information is provided for completeness of disclosure of the preferred embodiment and is not limiting inasmuch as any pressure sensor which gives an electrical output and which senses pressure in the 0 to 5 or 0 to 10 PSIG range may be used.

The sensor 60 is connected by means of electrical leads 62 which extend through aperture 64 in disks 66 to a cable 68. An insulator disk 70 protects the connections from the sensor to the cable from contact with the battery. A battery clip 72 is held in place by a keeper 74 received in apertures 76 on disk 66. At the other end of the battery B, another battery clip 78, secured in place by pin 80 to block 82, which is provided with an aperture 84 makes contact with the other end of the battery. A connector 86 extends through the aperture 84 and provides connection with the cable 68 and with the battery B. A circuit board connector 88 is in electrical communication with the connector 86 and connects the circuit board 90 electrically to the battery and to the sensor 60. The circuit board 90 is provided with a microprocessor 92, along with suitable interconnection circuitry, as is conventional in modern digital electronics. The microprocessor 92 is secured to the printed circuit board 90 by means of a pair of clips 94 and 96, 94 connecting one end of the microprocessor and 96 connecting the other end of the microprocessor and the clips 94 and 96 forming the electrical components of the switch which turns the display on and off. When assembled, the button 36 presses the release spring 96 which places it in electrical contact with the spring or strip 94 thus completing an electrical circuit through the microprocessor and the display.

A board 98 is also secured to the printed circuit board and is provided with a multiplicity of light-emitting diodes numbers 101 through 119. Typically, some of the light-emitting diodes are red and some are green, and one is white or yellow and is used simply as a control or pilot to show that the instrument is on or that there is electricity to the circuit board.

A mount 120 supports a potentiometer 122 which is connected by suitable connectors to the microprocessor and serves to zero the instrument.

Now, reviewing the entire description and drawing as described thusfar, it will be seen that the entire assembly can be held in the hand of the surgeon. He simply holds it in either his right or his left hand and watches the LED lights. When they light up beyond a given level, he knows that there is potentially an overpressure in the tissue. In the particular embodiment, the light 101 may be a yellow LED which is simply a pilot or indicator light to show that the instrument is ready for operation. The next five lights, 102 through 107, may be green lights indicating a safe or normal tissue fluid pressure range. The lights 108 through 119 are in the preferred embodiment red indicating that a higher pressure than is normal is being read. The lights may be calibrated to read in any increments. For example, each light may be calibrated to indicate an additional increase in pressure of 10 cm of mercury.

Thus, a very convenient, light, and versatile instrument which requires little space, is easily handled and easily read has been provided, thus obviating the difficulties faced by surgeons in using the prior art instruments.

INDUSTRIAL APPLICATION

This invention finds application in medicine and surgery and, in particular, in medical therapy of humans and animals.

What is claimed is:

1. In a tissue pressure measuring system which comprises a syringe having a cylindrical passage and means for connecting a tissue invasion device in fluid communication with the cylindrical passage, a plug in the cylindrical passage having a passage formed therethrough, means sealing the periphery of the plug in fluid tight moveable relationship with the interior of the cylindrical passage, a resilient pressure transmitting diaphragm sealing the passage through the plug and a cylindrical pressure measuring instrument connected to the plug for moving the plug in the cylindrical passage and for sensing pressure transmitted through the diaphragm, the improvement wherein the diaphragm is a membrane formed of inert resilient material fitted inside the interior of the plug, said diaphragm having a substantially flat center portion and an annular portion having a substantially arcuate cross-section around the center point.

* * * * *